United States Patent [19]

Koontz

[11] Patent Number: 6,022,902
[45] Date of Patent: Feb. 8, 2000

[54] POROUS ARTICLE WITH SURFACE FUNCTIONALITY AND METHOD FOR PREPARING SAME

[75] Inventor: Steven L. Koontz, Dickinson, Tex.

[73] Assignee: The United States of America as represented by the Administrator of the National Aeronautics and Space Administration, Washington, D.C.

[21] Appl. No.: 08/858,219

[22] Filed: May 14, 1997

Related U.S. Application Data

[63] Continuation-in-part of application No. 08/254,361, Jun. 3, 1994, Pat. No. 5,798,261, which is a continuation-in-part of application No. 07/857,901, Mar. 26, 1992, Pat. No. 5,369,012, and application No. 07/997,265, Feb. 23, 1993, Pat. No. 5,332,551, which is a division of application No. 07/894,505, Jun. 2, 1992, Pat. No. 5,215,790, which is a division of application No. 07/429,739, Oct. 31, 1989, Pat. No. 5,141,806.

[51] Int. Cl.$^7$ .................................. C08J 9/22; C08J 9/40; C08J 9/42
[52] U.S. Cl. .............................. 521/53; 428/543; 521/53; 521/59; 521/84.1; 521/143; 521/146; 521/149; 521/150; 525/54.1
[58] Field of Search ............................... 521/53, 59, 84.1, 521/146, 149, 150, 143, 155; 525/54.1; 428/543

[56] References Cited

U.S. PATENT DOCUMENTS

| | | | |
|---|---|---|---|
| 3,992,495 | 11/1976 | Sano et al. ................................. | 264/22 |
| 4,046,843 | 9/1977 | Sano et al. ................................. | 264/22 |
| 4,346,142 | 8/1982 | Lazear .................................... | 428/315.7 |
| 4,413,074 | 11/1983 | Wrasidlo et al. ......................... | 524/43 |
| 4,571,390 | 2/1986 | Sakagami et al. ....................... | 502/402 |
| 4,632,842 | 12/1986 | Karwoski et al. .......................... | 427/2 |
| 4,845,132 | 7/1989 | Masuoka et al. ......................... | 521/53 |
| 4,851,121 | 7/1989 | Yokota et al. ...................... | 210/500.36 |
| 5,108,607 | 4/1992 | Kraus et al. ........................ | 210/500.39 |
| 5,130,024 | 7/1992 | Fujimoto et al. ................... | 210/500.36 |
| 5,286,382 | 2/1994 | Scarmoutzos et al. .................. | 210/490 |
| 5,369,012 | 11/1994 | Koontz et al. .......................... | 435/7.92 |
| 5,531,899 | 7/1996 | Yen et al. ................................ | 210/638 |
| 5,543,054 | 8/1996 | Charkoudian et al. .................. | 210/638 |

FOREIGN PATENT DOCUMENTS

| | | |
|---|---|---|
| 60-221441 | 11/1985 | Japan . |
| 2-208333 | 8/1990 | Japan . |

OTHER PUBLICATIONS

Yao et al., "The influence of the Surface Cross–linking of the High Density Polyethylene Induced by Plasma Treatment on the Durability of Treatment Efficiency," *Journal of Applied Polymer Science*, 48:57–65, 1993.
Fujimura et al., "Resist stripping in an $O_2$ + $H_2O$ plasma downstream," *J. Vac. Sci. Technol.,* B9(2):357–361, Mar./Apr. 1991.
Chou et al., "Detailed model of the afterglow region of a microwave generated oxygen plasma," *J. Appl. Phys.* 72(3):870–878, 1992.
Deshmukh and Economou, "Remote plasma etching reactors: Modeling and experiment," *J. Vac. Sci. Technol. B,* 11(2):206–215, 1993.
Shard and Badyal, "Plasma versis ultraviolet enhanced oxidation of polyethylene," *Polymer Communications,* 32(7):217–219, 1991.
Koontz and Nordine, "The reaction efficiency of thermal energy oxygen atoms with polymeric materials," in Materials Degradation in Low Earth Orbit (LEO), 119th annual meeting of the Minerals, Metals & Materials Society in Anaheim, California, Feb., 17–22, 1990, pp. 189–205.
Badey et al., "A comparitive study of the effects of ammonia and hydrogen plasma downstream treatment on the surface modification of polytetrafluoroethylene," *Polymer* 37(8):1377–1386, 1996.
Wu et al., "Ammonia plasma treatment of Polyolefins for adhesive bonding with a cyanoacrylate adhesive," *J. Adhesion Sci. Technol,* 9(4):501–525, 1995.
Brennan et al., "Surface modification of ultra–high molecular weight polyethylene fibers by γ–radiation–induced grafting," *J. Adhesion Sci. Technol.,* 9(8):1031–1048, 1995.
Collaud et al., "Plasma treatment of polymers: the effect of the plasma parameters on the chemical, physical, and morphological states of the polymer surface and on the metal–polymer interface," *J. Adhesion Sci. Technol.,* 8(10):115–1127, 1994.
Egitto and Matienzo, "Plasma modification of polymer surfaces for adhesion improvement," *IBM J. Res. Develop.,* 38(4);423–439, Jul. 1994.
Foerch et al., "Modification of Polymer Surfaces by Two–Step Plasma Sensitized Reactions," *Journal of Polymer Science: Part A: Polymer Chemistry,* 28:803–809, 1990.
Foerch et al., A comparative study of the effects of remote nitrogen plasma, remote oxygen plasma, and corona discharge treatments on the surface properties of polyethylene,: *J. Adhesion Sci. Technol.,* 5(7):549–564, 1991.

(List continued on next page.)

*Primary Examiner*—Morton Foelak
*Attorney, Agent, or Firm*—Hardie R. Barr

[57] ABSTRACT

Porous organic articles having no surface functionality may be treated by remote plasma discharge to thereby introduce functionality to the surface of the article. The functionality is introduced throughout the article's surface, including the exterior surface and the surfaces of the pores. Little or no degradation of the porous organic article occurs as a result of the functionalization. Amino, hydroxyl, carbonyl and carboxyl groups may be introduced to the article. In this way, an essentially inert hydrophobic porous article, made from, for example, polyethylene, can have its surface modified so that the surface becomes hydrophilic. The remote plasma discharge process causes essentially no change in the bulk properties of the organic article. The remote plasma discharge process is preferably conducted so that no photons, and particularly no ultraviolet radiation, is transmitted from the plasma glow to the porous article. The surface-functionalized article may be used, for example, as a solid support in organic synthesis or in the chromatographic purification of organic or biochemicals.

19 Claims, 1 Drawing Sheet

OTHER PUBLICATIONS

Foerch et al., "Oxidation of Polyethylene Surfaces by Remote Plasma Discharge: A Comparison Study with Alternative Oxidation Methods," *Journal of Polymer Science: Part A: Polymer Chemistry*, 28:193–204, 1990.

Girardeaux et al., "Ammonia Plasma Treatment to Tailor Pet Polymer Surface Chemistry for Biomedical Applications," *Polymer. Prep.*, 36(1):91–92, 1995.

Gengenbach et al., "Restructuring of Polymer Surfaces Following Ammonia Plasma Treatment," *Polym. Prepr.*, 34(2):104–105, 1993.

Koontz et al., "The Materials Chemistry of Atomic Oxygen with Applications to Anisotropic Etching of Submicron Structures in Microelectronics and the Surface Chemistry Engineering of Porous Solids," in NASA Conference Publication 3263, 1994, pp. 354–367.

Koontz et al., "Intelsat Solar Array Coupon Atomic Oxygen Flight Experiment," *Journal of Spacecraft and Rockets* 31(3): 475–481, 1994.

Yasuda et al., "Plasma–surface Interactions in the Plasma Modification of Polymer Surfaces," in Polymer Surfaces and Interfaces, Feast and Munro (eds.), John Wiley & Sons Ltd., 1987, pp. 149–162.

6,022,902

1

POROUS ARTICLE WITH SURFACE FUNCTIONALITY AND METHOD FOR PREPARING SAME

CROSS-REFERENCE TO RELATED APPLICATIONS

This is a continuation-in-part of U.S. application Ser. No. 08/254,361 filed Jun. 3, 1994, U.S. Pat. No. 5,798,261 which in turn is a continuation-in-part of U.S. application Ser. No. 07/857,901, filed Mar. 26, 1992 now U.S. Pat. No. 5,369,012 and Ser. No. 07/997,265, filed Feb. 23, 1993 now U.S. Pat. No. 5,332,551, which in turn is a division of U.S. application Ser. No. 07/894,505, filed Jun. 2, 1992, now U.S. Pat. No. 5,215,790, which in turn is a division of U.S. application Ser. No. 07/429,739, filed Oct. 31, 1989, now U.S. Pat. No. 5,141,806.

STATEMENT OF GOVERNMENT INTEREST

The invention described herein was made by employee(s) of the United States Government and may be manufactured and used by or for the Government of the United States of America for governmental purposes without the payment of any royalties thereon or therefor.

FIELD OF THE INVENTION

This invention relates generally to porous articles, more specifically to porous articles formed from organic polymer and having functional groups at the surface thereof, and to methodology for preparing surface-functionalized porous articles using remote radical forming conditions.

BACKGROUND OF THE INVENTION

Porous solid materials are widely utilized in the synthesis and purification of organic and biochemicals. For example, the synthesis of biochemicals such as oligonucleotides and polypeptides can be done using solid phase supports in order to greatly reduce the time and expense arising from the inevitable purifications needed between intermediate steps in a multi-step chemical synthesis. The practice of solid phase synthesis is also particularly amenable to automation, thus allowing significant cost-savings in terms of labor. These advantages have prompted a great deal of research activity directed to improvements in solid phase synthesis, and one area of keen interest is the development of superior solid supports.

Many different solid supports are currently used commercially for separation or solid phase synthesis, and many more have been described in various patents and publications. In general, the efficiency of a solid phase synthesis and separation processes depends on the surface area of the solid phase material. Porous materials offer the advantage of higher surface area per unit volume than the corresponding full density solids, permitting vastly improved synthesis and separation performance per unit volume of solid material.

One popular solid support is made from glass or silica, typically in the form of beads. Glass beads have several desirable properties. For example, they are inert to most (although not all) chemical reactions, and they are not easily crushed. Glass has many surface hydroxyl groups that can be used as "chemical handles" to join molecular fragments to the glass. Glass is fundamentally inexpensive, and technology has developed that can make glass beads highly porous, so that the beads have a high surface area/volume ratio.

However, glass beads are also rather brittle, and thus not very stable to mechanical action. When placed into a con-

2 tainer with a mechanical stirrer, small pieces of the beads typically chip away, and these small pieces (commonly termed "fines") may find their way into the filtration equipment that is used to separate the beads from the spent reaction solutions. These fines can clog the filtration equipment, and thus present a continuing maintenance problem.

Although there are a large number of organic polymers, in the form of beads, membranes or monoliths, that are not brittle, thereby providing researchers with a potential means for solving the "fines" problem associated with glass beads, identifying an organic-based solid support with the correct balance of properties has proven to be a significant challenge. Typical methods to functionalize an organic polymer, i.e., provide the "chemical handles" that are needed to allow the polymer to serve as a solid-phase synthesis support or chromatography media, are rather harsh and lead to undesirable degradation of the polymer.

There is thus a need in the art for solid-phase supports for synthesis and separations which overcome the disadvantages of the prior art materials. The present invention fulfills this need and provides further related advantages as described herein.

SUMMARY OF THE INVENTION

The invention provides a porous article having an exterior surface, a bulk matrix and pores extending from the exterior surface into the bulk matrix. The pores define an interstitial surface. The bulk matrix is formed, at least in part, of an organic polymer comprising carbon and hydrogen atoms. The exterior and interstitial surfaces are formed, at least in part, of the same organic polymer comprising carbon and hydrogen atoms, which has been modified so that some of the hydrogen atoms are replaced with functional groups including amino, hydroxyl, carbonyl, and carboxylic acid. The invention provides a mild method of introducing functionality to a porous article, so that the exterior surface does not display surface roughness, according to SEM analysis, due to ablation of surface carbon atoms or chain scission.

Another aspect of the invention provides a process for introducing functionality to the surface of a porous article. The process includes providing a precursor porous article having an exterior surface, an interstitial surface and a bulk matrix, where the interstitial surface and bulk matrix both are formed, in whole or part, of organic polymers. The porous article is exposed to a remote discharge formed by radical forming conditions acting on a source gas, where the source gas may be oxygen, ammonia or a mixture of nitrogen and hydrogen. The porous article is exposed to the remote discharge under reaction conditions such that radicals from the discharge react with the organic polymers present at the exterior and interstitial surfaces of the precursor porous article. This reaction introduces direct covalent bonding of functionality to the surfaces, where the functionality may be amino, hydroxyl, carbonyl or carboxyl groups.

In one embodiment, the discharge used in the inventive process is a plasma discharge. In another embodiment, photons generated by the radical forming conditions, and particularly ultraviolet radiation, do not contact the precursor porous article. Subsequent to being exposed to the discharge, the surface-functionalized porous article having carbonyl and carboxylic acid groups (possibly in addition to hydroxyl groups) may be reacted with a reducing agent, so that hydroxyl groups are the predominant functional group bonded to the polymers which form the surface of the article.

In addition, or alternatively, chemical agents that react with and cap (neutralize, eliminate) surface free radical sites and/or peroxides are contacted with the surface functionalized porous article. Such chemical agents include ammonia, dimethyl sulfide and other gases known in the art to cap/react with/neutralize free radical or peroxides on a polymer surface.

Another aspect of the invention provides a surface-functionalized porous article prepared by a process which includes providing a precursor porous article having an exterior surface, an interstitial surface and a bulk matrix. The surfaces and bulk matrix are formed, in whole or part, of organic polymers. The porous article is exposed to remote discharge formed by radical forming conditions acting on a source gas. The source gas may be oxygen, ammonia or a mixture of nitrogen and hydrogen. The porous article is treated under reaction conditions such that radicals from the discharge react with the surfaces of the precursor porous organic article to cause direct covalent bonding of functionality to the surfaces, where the functionality may be amino, hydroxyl, carbonyl or carboxyl groups.

In a preferred embodiment, analysis for surface functional groups introduced by the process described above shows that the same useful functional group concentration is present throughout the entire interstitial surface of the porous solid. The exterior pore surfaces preferably have the same or essentially the same morphology and functional group concentration as the internal pore surfaces. The internal and exterior pore surfaces of the porous articles of the invention show essentially the same morphology by SEM as the starting porous material for the process. Thus, the exterior pore surfaces and internal pore surfaces contain little or no degradation from: 1) UV/VUV photochemical degradation, 2) ion and electron impact processes, 3) chemical etching.

Polyolefin, and particularly polyethylene, is a preferred material from which the article is formed. Thus, the invention provides for porous articles having amino-substituted polyethylene forming the exterior and interstitial surfaces, and unsubstituted polyethylene underlying the surfaces. In another embodiment, the invention provides for porous articles having hydroxyl-substituted polyethylene forming the exterior and internal pores surfaces, and unsubstituted polyethylene underlying the surfaces. The surface amine and hydroxyl groups are distributed throughout the surfaces of the article, including the surface of the innermost pores.

These and other aspects of this invention will become apparent upon reference to the following detailed description and attached drawings.

DESCRIPTION OF THE INVENTION

Figure 1:
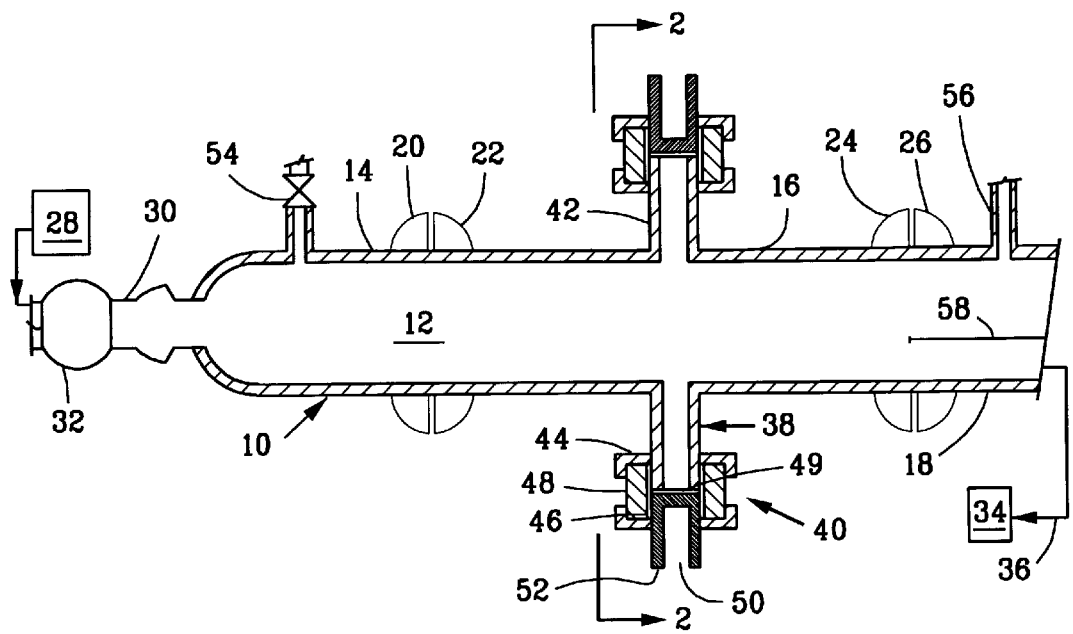
FIG. 1 is a schematic cross-sectional view of a sidearm reactor according to the present invention.

As briefly stated above, the present invention provides a method for introducing functionality onto the interstitial surface of a porous article, and further provides porous articles having surface functionality distributed throughout the exterior and interstitial surfaces of the article. The surface functionalized porous article may be prepared using remote plasma discharge or other gas radical forming conditions.

POROUS ARTICLES

The following general nomenclature is useful in describing the porous article of this invention. Various portions of the surface of a porous article may be distinguished from one another depending on location, chemical reactivity, responsiveness to various analytic techniques, etc. For example, a porous article has an exterior surface, by which is meant the surface which is actually visible using a microscopic technique, such as scanning electron microscopy, without having cut or sectioned the article. The porous article contains pores, which extend from the exterior surface into the bulk matrix. The porous article thus has pore surfaces, which are essentially the surfaces that surround and define the pores of the article. The pore surfaces may sometimes be referred to as the interstitial surface because they surround the interstitial volume of the porous article, where the interstitial volume is all of the volume within the article that is not formed of organic or inorganic material.

Some fraction of the pore surface is visible using microscopy to examine the porous article, and thus the exterior surface includes a fraction of the pore surfaces, called the exterior pore surfaces. However, the majority of the pore surfaces is typically buried within the porous article, and is not visible by microscopy unless the porous article is cut or sectioned to reveal the internal pores. This major portion of the pore surfaces, which is not visible by scanning electron microscopy, is called the internal or interstitial pore surface of the porous article. Thus, the surface of a porous article includes an exterior pore surface and an internal or interstitial surface.

In terms of volume, the porous article may be seen as having an interstitial volume, which is defined as essentially all of the volume within the article that would be accessible to a fluid that entered the article, i.e., the volume surrounded by the pore surfaces which does not contain the organic or inorganic material that forms the article. The interstitial volume may also be called the void volume. The volume of the article which is formed of organic and inorganic material, and which does not include the surface of the article, is referred to herein as the article's bulk matrix, or alternatively the polymer matrix or the bulk volume of the article. The portion of the article's bulk matrix which is present at or within 1,000 angstroms of the surface will be referred to herein as forming the near surface region. The portion of the porous article that does not form either the interstitial volume, the surface or the near surface region will be referred to as the interior bulk matrix of the article. With this nomenclature, porous articles useful in, and formed according to the present invention may now be described.

Porous articles useful in the invention are formed, in whole or part, of organic polymer, i.e., carbon and hydrogen containing polymers. Preferably, the porous article is formed entirely from organic polymer. However, the porous article may be a composite of inorganic material and organic polymer. When the porous article is a composite, then at least some of the surface of the article is formed of organic polymer, and preferably at least some of the bulk matrix is formed of the same organic polymer. A preferred composite article has a surface that is entirely formed of organic polymer, and more preferably has a bulk matrix that is predominately organic polymer.

Because the invention provides a very mild method of introducing functionality onto the surface of an organic polymer, essentially any organic polymer having hydrogen atoms may be treated according to the inventive method. The polymer can be a synthetic, semisynthetic, or naturally occurring organic polymer. For instance, the organic polymer which forms the porous article may be a hydrocarbon, in which case the porous article will have hydrophobic properties. Preferred hydrocarbon polymers are formed from olefin, i.e., the polymer is a polyolefin. Suitable hydrocarbon olefins from which the article may be made include, without limitation, ethylene, propylene, butylene, butadiene, styrene, α-methylstyrene, divinylbenzene and the like, although preferred hydrocarbon olefins do not contain aromatic rings. Hydrocarbon polymers are well known in the art, and are listed in, e.g., The Polymer Handbook, $3^{rd}$ Edition, Brandrup, J. et al. (eds.) John Wiley & Sons, Inc., New York, N.Y. (1989). Articles formed in whole or part from polyethylene are preferred starting materials in the inventive process, and more preferably the porous article is formed entirely of polyethylene. In general, polymers that are inherently hydrophobic in bulk form are preferred materials for forming the porous article. Hydrophobic polymers include hydrocarbons, PTFE, polyacrylonitrile, polyetherimide, polysulfone, and polyethersulfone.

The polymer may contain heteroatoms such as halogen, silicon, sulfur, oxygen and/or nitrogen atoms, as present in, e.g., polyamide, polyvinylchloride, polyurethane, polyacrylate, phenolic resins alkyd resins, polyester, cellulose, starch, polysaccharide, polypeptide, rubber, gutta percha, poly(ethylene terephthalate), polyimide, polytetrafluoroethylene, poly(vinylidene fluoride), polysulfone, poly(ether sulfone), Kynar™, PEEK, Tefzel™, Teflon™, polydimethylsiloxane, polyphenylsiloxane, dimethylsiloxane/methylvinylsiloxane, copolymer, substituted polyphosphazenes, and the like. When heteroatoms are present in the polymer's repeating unit, the repeating unit preferably contains more carbon atoms that non-carbon atoms (excluding hydrogen and halogen atoms). Again, polymers containing heteroatoms which may be used according to the present invention are well known in the art, and are listed in, e.g., The Polymer Handbook (supra).

The inventive process is generally applicable to all organic polymers. Accordingly, the polymer from which the article is formed may have any molecular weight, molecular weight distribution, stereochemical configuration or conformation, degree of crosslinking, density, tensile strength, extent of entanglement, glass transition temperature (although this should be above room temperature, so that the article is a solid at room temperature), tacticity, melt viscosity and color, among other properties that characterize polymers.

Preferably, the polymer has a relatively high molecular weight, on the order of 1,000,000 daltons or more (number average molecular weight). When the polymer has a relatively high molecular weight, there tends to be a greater degree of entanglement among the polymer chains. This greater degree of entanglement tends to inhibit the polymer chains from moving around within the article. Consequently, functionality which is initially introduced to the surface of a porous article will tend to remain at that surface for a longer period of time when the average molecular weight of the polymer chains is relatively high.

As stated above, polyethylene is a preferred polymer from which the article is formed. So-called ultra-high molecular weight polyethylene (UHMWPE) is a preferred polyethylene. UHMWPE is described in, e.g., U.S. Pat. No. 5,531,899. Polyethylene is typically characterized in terms of its density, and both high density and low density polyethylene may be used to form the porous article.

The article which is functionalized according to the inventive method is porous. Preferably, the article is characterized by a plurality of interconnected pores on a larger-than-molecular scale. The article may also be described as permeable, in that the pores are interconnected to allow fluid flow from an exterior surface into an adjacent region in the structure, and from one adjacent region to another. Preferably, the pores are interconnected so that fluids may flow throughout the article. The pores may be isotropic or anisotropic, and may be nondirectional or unidirectional, to name a few of the ways in which porous articles may be characterized. The pores may be connected by a so-called tortuous path, which essentially means that the pore channels are randomly directed through the article in a nondirectional manner.

However, the pores need not be interconnected but instead may be separate from one another. For example, the pores may be separate from one another but extend completely through the article, or the pores may terminate within the porous article, where the later situation provides for so-called "non-through" pores. However, the pores should be accessible to fluids that contact the exterior surface of the porous article, i.e., the porous article should not a closed cell foam or the like where all of the pores are isolated from the exterior surface.

The porosity of the article may be characterized in terms of pore diameter and void volume. The pores generally have effective diameters larger than about 0.01 microns (1 angstrom), preferably at least about 1 micron up to about 2000 microns, and more preferably from about 10 to about 1000 microns. Thus, the porous article can be distinguished from semipermeable solid-phase membranes which generally have intermolecular openings on a molecular size scale for molecular diffusion. The porous article may be microporous, in which case the article has a pore size in the range between about 0.05 and about 20 microns. The porous article may be macroporous, in which case the article has a pore size of about 20 microns to about 2000 microns, preferably about 20 to 500 microns. A preferred porous article has an effective pore size of about 1 to about 50 microns. Porosity may be determined according to ASTM D276-72, and pore size distribution may be determined according to ASTM F316-70.

The porosity of the article can also be characterized in terms of pore volume. Thus, the porosity may be defined as the pore volume divided by the total volume of the article. In percentage terms, porosity refers to the pore volume as defined above, multiplied by 100. While porous articles of any pore volume from 1% to 90% may be used in the present invention, preferred porous articles have a pore volume of about 20% to about 80%, more preferably have a pore volume of about 30% to about 70%, and still more preferably have a pore volume of about 35% to about 60%.

Porous articles may be made by methods which are well known in the art. The variety of techniques which are described in Kesting, Robert E., *Synthetic Polymeric Membranes*, John Wiley & Sons, New York, 1985, pp. 237–309, which is hereby incorporated herein by reference, are exemplary. The pores may be introduced by mechanical perforation, by the introduction of pore producing agents (e.g., porogens) during the matrix forming process, through various phase separation techniques, or other methods. Indeed, the manner in which the article is made porous is not especially important to the practice of the present invention. However, the properties of the porous material should be selected so that the article has the necessary porosity, strength, durability and other properties which render it suitable for the intended application. The porous article is preferably self-supporting.

A porous material which is prepared by sintering together finely divided polymer particles (i.e., particulated polymer)

has been found to have very good physical properties for a number of applications, including use as a solid support for organic synthesis and chromatography. See, e.g., U.S. Pat. No. 3,051,993. The polymer particles may or may not be porous in and of themselves. However, the material formed by sintering the polymer particles will have void volume between the sintered particles, where that void volume creates interstitial surface. Such materials are referred to herein as sintered articles, e.g., sintered polyolefin if the polymer particles are made of polyolefin. A porous material prepared by sintering non-porous polyolefin particles (typically beads) is a preferred porous material according to the invention, and for articles made from polyethylene, is commercially available from, e.g, Porex Technologies USA (Fairburn, Ga.) under their trade designation POREX™.

The porous article may have essentially any shape. For example, the article may be in the shape of a cube, block, sphere, tube, rod or cylinder, sheet, disc, membrane, film, monolith or the like. Articles in the form of a block/cube or rod/cylinder are preferred for many applications, and may be obtained from Porex Technologies USA (Fairburn, Ga.). A preferred article in the form of a film is porous polyethylene film, e.g., CELGARD™ K-878, which is commercially available from Celanese Corporation (Norristown, N.J.). Microporous polymeric films which may be treated according to the invention are described in, e.g., U.S. Pat. Nos. 3,839,516; 3,801,404; 3,679,538; 3,558,764 and 3,426,754.

The article may be a composite of two polymers. An exemplary composite is a breathable, hydrophobic polysiloxane membrane reinforced with poly(tetrafluoroethylene) which is sold under the tradename SILON™ by Bio-Med Sciences, Inc. (Bethlehem, Pa.). These membranes are typically used as wound dressings, gas and fluid exchange membranes, etc. The article may have a shape resulting from drawing, molding, sintering, or other polymer processing step.

REMOTE RADICAL FORMING CONDITIONS

The invention provides a process wherein reactive gas-phase radicals and a porous article (hereinafter "the specimen") are present within a single reactor, such that the radicals contact the specimen and create functionality throughout the surface of the specimen. The radicals are generated from a source gas, in a non-equilibrium, low pressure environment, and delivered to the specimen by at least one of convective and diffusional transport. The radicals are generated from the source gas by exposing the source gas to so-called "radical forming conditions" as created by, for example, a radiofrequency (RF), microwave or direct current discharge (any of which will create a gas plasma discharge), laser sustained discharges, UV laser photolysis, high-powered UV/VUV lamp driven photolysis, high energy electron beams, and other high-intensity ionizing or radical forming radiation sources. While any of these radical forming conditions may be used to generate the reactive radicals, gas plasma discharge is a preferred technique.

The source gas according to the present invention comprises oxygen, ammonia, or a mixture of nitrogen and hydrogen. Preferably, oxygen and ammonia are not used simultaneously, and the mixture of nitrogen and hydrogen is not used with either oxygen or ammonia. These source gases may be used in pure form (i.e., above about 95% purity) or in dilute forms, where suitable diluent gases include helium, argon and nitrogen. Diluted source gases afford the advantage that reactive radicals that are generated from dilute oxygen, nitrogen or ammonia demonstrate fewer recombination events, thus providing for a longer-lasting and higher concentration of reactive radicals in the reactor. In addition, the energy transferred from an excited metastable species formed from a diluent gas, e.g., Ar*, can increase the yield of the reactive radical.

For example, 10% oxygen in argon at a pressure of 2 Torr provides about the same ability to functionalize a porous specimen as does pure oxygen. Argon is a preferred diluent gas because the metastable electronic excited state of argon promotes dissociation of molecular oxygen or ammonia by collisional energy transfer, and so promotes in-plasma dissociation kinetics. Thus, dilute gases having about 10% concentration of oxygen or ammonia are preferred according to the invention.

When oxygen serves as the source gas, the reactor of the invention converts the oxygen ($O_2$) to atomic oxygen radical ($O_2$). With the reactor and operating conditions as described herein, the minimum concentration of atomic oxygen radical within the reactor (at the location where the atomic oxygen contacts the specimen, and at 298° C.) is preferably at least $1 \times 10^{13}$ atoms/cc, as measured by $NO_2$ chemiluminescent titration (as described in, e.g., Kaufman, F., *Progress in Reaction Kinetics*, vol. 1, Pergamon Press, London, pp. 1–39, 1961). In addition to atomic oxygen, hydroxyl radicals will also typically react with the specimen. This is due to the fact that one possible reaction that can occur when atomic oxygen contacts the specimen is the formation of hydroxyl radical. This hydroxyl radical is then available to react with the specimen. In one embodiment of the invention, a "sacrificial" polymer may be placed upstream of the specimen, in order to enhance the concentration of hydroxyl radicals that react with the specimen.

When ammonia serves as the source gas, two reactive radicals are generated: hydrogen ($H_1$) and amino ($NH_2$). While not intending to be bound by any theory, it is believed that hydrogen radicals initially react with the specimen to abstract a hydrogen radical and thereby form hydrogen gas. The residual radical site on the specimen then reacts with an amino radical to place an amino group on the specimen. In any event, with the reactor and operating conditions as described herein, the minimum concentration of atomic hydrogen radical within the reactor (at the location where the atomic oxygen contacts the specimen) is preferably at least $1 \times 10^{16}$ atoms/cc at a temperature of 298° C., as measured by NO chemiluminescent titration (as described in Kaufman 1961, supra) and calculated from the pressure rise seen on ignition of the plasma source. This minimum value is preferably maintained regardless of the working pressure.

It is often the case, particularly when using oxygen as the source gas, that undesirable by-products are produced along with the desired gas-phase radicals, where the by-products may be undesirable because they can cause damage to the specimen. Such by-products include electrons, ions and UV radiation. Thus, the preferred reactor provides an environment which precludes, or at least substantially precludes, contact between the specimen and undesirable by-products. Preferably, the reactor allows the undesirable by-products to undergo natural decay prior to their contacting the specimen. In other words, the preferred reactor and operation thereof provides that a specimen is exposed to an environment wherein the rate of decay of desired gas-phase atomic and molecular radicals is much less than the decay rate of undesirable by-products. This environment provides for "remote" treatment of a specimen using radical forming conditions.

The terms "remote plasma", "downstream plasma", and "flowing discharge" are generally synonymous. Techniques to achieve remote plasma discharge are described in, e.g., Foerch, R. et al. "A comparative study of the effects of remote nitrogen plasma, remote oxygen plasma, and corona discharge treatments on the surface properties of polyethylene" *J. Adhesion Sci. Technol.* 5(7):549–564 (1991); Deshmukh S. C. et al. "Remote plasma etching reactors: modeling and experiment" *J. Vac. Sci. Technol. B*, 11(2):206–215 (March/April 1993); Boitneott, C. "Downstream plasma processing: considerations for selective etch and other processes" *Solid State Technology*, pages 51–58, October 1994; Brady J. P. et al. "A comparative study of the effects of ammonia and hydrogen downstream plasma treatment on the surface modification of polytetrafluoroethylene" *Polymer* 37(8):1377–1386 (1996). These publications are hereby incorporated by reference herein.

As used herein and in the above publications, the terms "remote plasma" and "downstream plasma" generally refer to an environment wherein the substrate being modified by the plasma is located such that the substrate is not exposed to plasma-derived species that can cause collateral damage to the substrate. Remote or downstream plasma techniques (hereinafter, simply "remote plasma") described in the literature, which are directed, for example, to etching processes in the semiconductor industry, or otherwise modifying the surface of a substrate, may be used in the process of the present invention so long as they achieve little (less than 10% mass loss) or essentially no (less than 1% mass loss) collateral damage to the substrate while achieving complete functionalization of the surface of the porous article. Complete functionalization of all pore surfaces, both internal and external (external pore surfaces may be seen from visual examination of the exterior surface of the porous article), occurs when all pore surfaces, both internal and external, have been modified in the desired way and to a useful extent as described herein.

Because there is so little mass loss, there is little or no deviation in the pore size as measured on the surface of the article, compared to the average diameter of the pores within the matrix of the material (assuming, of course, that there was little or no deviation in the pore size of the specimen). Thus, porous articles having essentially the same pore diameters throughout the article, as well as articles having average pore diameters that deviate by no more than 1% or 2% between the exterior surface and the interior matrix, can be prepared according to the invention.

While remote plasma techniques described in the literature typically separate the specimen being treated from direct contact with the glow discharge plasma, it is not always the case that the specimen is spared contact with light that is emitted from the glowing discharge. In remote treatment according to a preferred embodiment of the present invention, photons emitted from the excited gas, and particularly UV radiation, do not contact the porous article.

Figure 2:
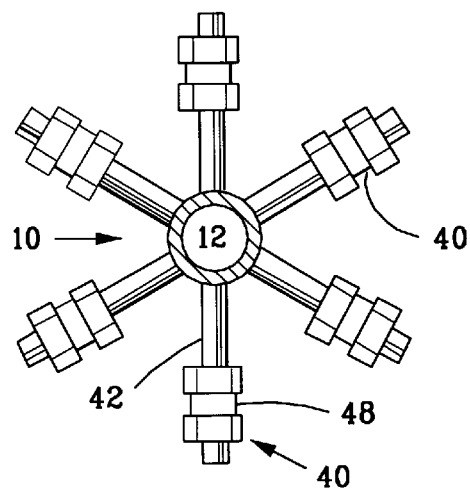
FIG. 2 is a cross-sectional view of the sidearm reactor of FIG. 1, as seen along the lines 2—2.

A preferred reactor, for process optimization studies, which may be used to produce a remote plasma environment according to the present invention is the atomic oxygen reactor having at least one sidearm conduit, which is described in U.S. Pat. No. 5,332,551 to Steven L. Koontz. When operated as described herein, this atomic oxygen reactor is used to achieve flowing discharge radical chemistry (FDRC) to modify the surfaces of porous articles. A preferred embodiment of an atomic oxygen reactor having at least one sidearm conduit (hereinafter, a "sidearm reactor") is illustrated in FIGS. 1 and 2 set forth herein, and may be operated as described below. Further description of the sidearm reactor and its operation appears in Koontz, S. L. et al. "The reaction efficiency of thermal energy oxygen atoms with polymeric materials", *Materials Degradation in Low Earth Orbit*, Srinivasan V. et al. eds., pages 189–205, The Minerals, Metals & Materials Society (1990) (Published proceedings of a symposium sponsored by the TMS-ASM joint corrosion and environmental effects committee, held at the 119$^{th}$ annual meeting of The Minerals, Metals & Materials Society, Feb. 17–22, 1990), which is hereby incorporated by reference herein in its entirety.

As shown in FIG. 1, a sidearm reactor 10 comprises a longitudinally oriented flow chamber 12 formed from three sections, namely an inlet section 14, a mid-section 16 and an exhaust section 18. These sections are secured together using conventional coupling flanges 20, 22, 24, and 26. Glass is a preferred material from which to construct the flow chamber 12. The reactor 10 further comprises an inlet line 28 through which the precursor to the reactive gas-phase radical (also termed a "source gas") may be introduced to the discharge generating apparatus 32. The apparatus 32 generates a plasma discharge that converts the source gas into a collection of reactive gas-phase radicals, as well as undesirable byproducts (collectively a flowing discharge gas). The flowing discharge gas exits the discharge generating apparatus 32 through the line 30 and passes into the inlet section 14 of the flow chamber 12.

The discharge generating apparatus 32 comprises a power supply and a cavity configuration wherein the source gas is exposed to a discharge. The cavity should afford a configuration of an electric field such that conducting surfaces are configured to produce a standing wave EM field. Suitable microwave discharge cavities are described in, e.g., Fehsenfeld, F. C., et al. *The Review of Scientific Instruments* 36(3):294–298 (March 1965). Suitable power supplies include any radiofrequency (RF), microwave or direct current power supplies. A suitable microwave power supply may be obtained from, for example, Raytheon Corporation, and identified under their trade designation as a Raytheon PGM-10. The Raytheon PGM-10 may be used in conjunction with an Evensen-type discharge cavity. The apparatus 32 may also consist of an ASTEX S-250 microwave power supply in conjunction with an ASTEX DPC24 plasma head which creates a cavity wherein the plasma is formed. The ASTEX components are available from Applied Science and Technology, Inc., Worburn, Mass. Either of these configurations may be used with any source gas of the invention. These power supplies are typically operated at (FCC-approved) 2.450 MHz, although the FCC also approves the use of 13 MHz band for industrial processing, and this could also be employed in the present invention.

Along the mid-section 16, and extending transversely to the longitudinal axis of the flow chamber 12, are one or more sidearms 38. The six sidearms of an exemplary reactor 10 are shown in FIG. 2. At the distal end of each sidearm 38 is a specimen holder 40 which holds the specimen 49 to be modified by the reactive gas-phase radicals. The sidearm 38 also comprises a sidearm conduit 42 which provides fluid communication between the specimen holder 40 and the mid-section 16 of the flow chamber 12. The sidearm conduit 42 is preferably constructed from glass.

The specimen holder 40 can be made by modifying a CAJON brand union fitting (Cajon Company, Macedonia, Ohio). Drilling can be used to remove the internal lips of the fitting while leaving the O-ring vacuum seals 44, 46 at either end of a sleeve member 48 adjacent the conduit 42. Each specimen holder 40 may also include a specimen heater well 50 and a thermocouple well 52. The specimen 49 which undergoes surface-modification is placed at the distal end of the conduit 42, inside the sleeve member 48.

The exhaust section 18 of the flow chamber 12 is in fluid communication with a vacuum pump 34 via line 36 positioned therebetween. Optionally, a catalytic atomic oxygen or atomic hydrogen probe (shown by feature 58) may be positioned within the discharge section 18, to thereby measure the concentration of the atomic oxygen exiting the flow chamber 12. A suitable catalytic atomic oxygen probe may be prepared by wrapping fine silver wire or thin foil around a low thermal rated type J or K thermocouple probe (from, e.g., Omega Scientific). A palladium probe may be used to measure hydrogen. A capacitance manometer connection (shown by feature 56) may also, or alternatively, be connected to the discharge section 18 in order to measure the pressure within section 18.

The reactor 10 is constructed and operated so that no significant radial concentration gradients of reactive gas-phase radicals exist within the sidearms. This is achieved, in part, by positioning the specimens within sidearms so that they are not subject to the direct flow of the glow discharge plasma generated by the discharge generating apparatus. The specimens are thus positioned so as not to be in direct contact with the plasma and so that photons from the plasma cannot reach the specimen.

The environment within the sidearms is preferably selected to deliver a uniform dose of reactive gas-phase radicals to the specimen(s). The term "uniform dose" means that the surface flux of radicals is essentially constant across the diameter of a sidearm. A uniform dose typically does, but need not, achieve a uniform spacing of induced functionality across the surface of the specimen. In addition, the environment should be such that the gaseous reactive radicals are able to diffuse to the surface of a specimen, and diffuse into the pores of a porous specimen. In this way, the radicals are able to penetrate deeply into the interstitial volume of a porous specimen. Such an environment can be used to provide for variable (low to high) levels of surface functionalization, with a uniform distribution of the functionality across the surface.

Concurrent with surface functionalization, the sidearm environment minimizes, and may essentially eliminate, specimen degradation. Thus, the inventive process introduces functionality to the surface of a porous article while causing very little change in the pore volume of the article. Thus, surface-functionalized porous articles may be prepared having pore volumes which are within 10% of the pore volume of the precursor porous article, and are preferably within 5% of the initial pore volume. When ammonia is the source gas, surface-functionalized porous articles may be prepared having pore volumes which are within 5% of the pore volume of the precursor porous article, and are preferably within 1% of the initial pore volume.

This lack of surface degradation is a desirable feature of the present invention. Known methods to introduce functionality to a polymer, such as direct plasma treatment or solution-phase chemical oxidation, typically cause a substantial amount of chain scission and ablation of carbon atoms at the surface of the article. These effects are readily seen by scanning electron microscopy, where they give rise to surface roughness. The present invention achieves surface functionality throughout the entire surface of a porous article, while not causing much, if any, change in the morphology of the surface. Thus, in functionalized porous articles prepared by the present invention, the pore surface appears substantially the same as the exterior surface, as viewed by scanning electron microscopy.

Remote plasma treatment according to the invention is achieved by proper selection of the reactor, including reactor dimensions and the materials from which the reactor is constructed, and proper selection of reactor operating conditions. These selections are not independent, and thus one selection must be made in view of the other. The following guidelines are useful in developing reaction conditions useful in the present invention.

Ultimately, in order to provide a uniform flux of reactive gas-phase radicals across the surface of a specimen, the selections are made so that the diffusional relaxation time (a characteristic time for gas diffusion to eliminate gas radical concentration gradients) of the reactive radicals within the sidearms is much smaller than the characteristic decay time(s) of the gas-phase radicals as resulting from the sum of all surface and gas-phase loss processes. These diffusional relaxation and decay times will depend on the dimensions of the sidearms, the reactivity of the materials from which the sidearms were constructed, the reactivity of the specimen, the total working pressure within the reactor, as well as the temperature within the reactor.

The upper and lower limits on the working gas pressure are determined by the need to provide enough of the specific reactive gaseous radicals of interest to complete the desired surface chemistry on the specimen in a reasonably short length of time. A reaction time of 1 minute or so, for a sample that is about 1 cm thick, is typical, although this time is highly dependent on the porosity of the specimen, and the average diameter of the pores. Highly porous samples, with small pore diameters, which characterizes many membranes, may require a reaction time on the order to 60 minutes or so. If the pressure is too high, for instance more than about 10 Torr (1300 Pa), then gaseous radical recombination reactions proceed at an undesirably fast rate, and rapidly deplete the reactive radical population. If the pressure is too low, say less than 0.1 Torr, then the number of gas phase radicals in the sidearm is too low to be practically useful. A working gas pressure between about 0.1 and 10 Torr (roughly 10 to 1300 Pa) is thus practically useful, with gas pressures of about 0.5 to 5 Torr (roughly 50 to 500 Pa) being preferred regardless of the source gas.

An important factor limiting the use of higher pressures is the increasing heat capacity of the gases at higher pressures. It is known that plasma discharges at atmospheric pressure produce high enthalpy gas streams which may vaporize metals and destroy polymers via purely thermal processes. Accordingly, as the pressure increases inside a reactor according to the invention, the temperature of the flowing gases increases, rapidly approaching the thermal limits of the apparatus. Operating conditions and pressures which would expose the specimen to temperatures in excess of 200° C. are generally not preferred. Preferred temperatures around the specimen are described below. As the effect of pressure on heat capacity depends to some extent on the identity of the source gas, the optimal working pressure is dependent on the choice of source gas.

The upper and lower limits on the working temperature within the sidearm are essentially determined by balancing desired reaction rate with rate of undesired specimen decomposition (decomposition occurs, for example, by ablation of carbon atoms from the polymer, typically with the formation of carbon dioxide). For oxygen source gas, a temperature of about 300 K affords a desired reaction rate that is much greater than the decomposition rate, and a typical specimen will undergo complete reaction in a matter of minutes. As the working temperature is lowered, the desired reaction rate is even more favored in comparison to the decomposition rate, (the decomposition rate becomes very slow), however the desired reaction rate also slows down, and thus lower temperature necessitate longer reaction times to prepare the desired sample. At higher temperatures, full functionalization of a specimen is more rapid, however specimen decomposition becomes noticeable. Accordingly, a working temperature of less than about 350 K is preferred, with a temperature range of about 250 K to about 325 K being more preferred, and a temperature range of about 275–310 K being still more preferred, when oxygen is the source gas.

When ammonia is the source gas, the activation energy for sample decomposition is very much greater than the activation energy for the desired reaction. Accordingly, ammonia allows for a wider latitude in the selection of the working temperature because the rate of the desired reaction will almost always be much greater than the rate of the undesired decomposition reactions. Thus, when ammonia is the source gas, relatively high temperatures are desirably used, for the reason that preparation of the fully functionalized specimen is completed more rapidly. A working temperature of about 275 K to about 400 K is preferred when using ammonia as the source gas, with a working temperature of about 300 K to about 375 K being more preferred, and a working temperature of about 325 K to about 350 K being still more preferred. While temperatures higher than 400 K can be used with ammonia, very little increase in the desired reaction rate is observed compared with using 300 K, and thus for reasons of economy and safety, a lower temperature is preferred. At temperatures lower than about 275 K, the rate of specimen functionalization using ammonia becomes undesirably slow from a commercial point of view.

The dimensions and configurations of a practical commercial reactor to accomplish remote plasma discharge reaction are selected while keeping the above temperature and pressure limits in mind, and can be designed using process data generated with the side-arm reactor. Thus, the convective flow time between the end of the plasma zone (feature 30 in FIG. 1) and the beginning of the remote plasma treatment section (feature 32 in FIG. 1) is preferably greater than $1 \times 10^{-4}$ seconds when the operating pressure is on the order of 1–2 Torr. Adjustments to the total mass flow rate of the gas and the pumping speed of the vacuum system allows variation of both the total pressure within the reactor and the residence time of the radicals. In general, as the mass flow rate is increased for a constant pump speed, the convective flow time of the radicals increases and the pressure increases. However, as the pump speed is decreased while the mass flow rate is kept constant, the pressure increases while the convective flow time also increases. Suitable operating conditions and reactor dimensions include an operating pressure of 1–2 Torr, an operating temperature of 298–325 K, a sccm of 125–135 and a distance of about 4 inches (about 10 cm) from the end of the plasma zone to the beginning of the remote plasma treatment section.

Given these pressure and temperature ranges, the diameter of the sidearm may be selected based on the equations that predict the diffusional relaxation and chemical recombination times of radicals within a sidearm As stated above, the sidearms 38 are constructed and operated so that no significant radial concentration gradients exist and a uniform dose of reactive gas-phase radical is thereby delivered to the specimen surface 49 which is held or secured transversely in the specimen holder 40. The elimination of radial concentration gradients in the sidearms 38 is determined according to well known gaseous chemical kinetic analysis, by determining the relative magnitude of two characteristic relaxation times, $T_{diff}$ and $T_{rcm}$, where $T_{diff}$ is the characteristic diffusional relaxation time for the sidearm 38 and $T_{rcm}$ is the time required for all reactive radicals in a sidearm to recombine. When $T_{diff}$ is much less than $T_{rcm}$, (e.g., $T_{diff} > 0.1 T_{rcm}$), then no significant radial concentration gradients exist and a uniform dose of reactive radical is delivered to the specimen surface.

$T_{diff}$ is determined according to the equation:

$$T_{diff} = R^2/D$$

wherein R is the radius of the sidearm 38 and D is the diffusion coefficient of the reactive radical (about 120 cm²/s in air at 65 Pa when the reactive radical is atomic oxygen). Diffusion coefficient values for other gases and pressures may be obtained from the published literature, and/or calculated based on basic gas kinetic theory.

The chemical recombination (relaxation) time, $T_{rcm}$, is determined according to the equation:

$$T_{rcm} = R/r_c v$$

wherein $r_c$ is the faction of reactive radicals which recombine or are otherwise lost upon striking the sidearm surface. A description of radical recombination may be found in, e.g., Smith, W. V. "The surface recombination of H atoms and OH radicals" *J. Chem. Phys.* 11:110–124 (March, 1943) and Krongelb, S. et al. "Use of paramagnetic-resonance techniques in the study of atomic oxygen recombinations" *J. Chem. Phys.* 31(5):1196–1210 (November, 1954), both hereby incorporated herein by reference. More generally, $r_c$ is the probability of the loss of a reactive radical from the population of reactive radicals, due to any first order or pseudo first order process. Such first order and pseudo first order processes include an atom or radical striking the sidearm wall or specimen within the sidearm, as well as the recombination of reactive radicals. The value of $r_c$ is about $3.2 \times 10^{-4}$ in the case of atomic oxygen, and $2 \times 10^{-5}$ for hydrogen, with a sidearm constructed from glass. The parameter "v" is the mean thermal speed of the reactive radical (about $6.3 \times 10^4$ cm/s at 300 K for atomic oxygen, about $6.5 \times 10^4$ cm/s at 300 K for ammonia and about $25.2 \times 10^4$ cms at 300 K for hydrogen). Thus, when R=1 cm and the reactor is operated at 65 Pa and 300 K, $T_{diff}$ is about 0.008 seconds and $T_{rcm}$ is about 0.1 seconds for atomic oxygen, so that $T_{diff}$ is less than $0.1 \times T_{rcm}$.

The sidearm reactor as described herein can be used to provide a predetermined, uniform dose rate of reactive radicals across a specimen surface. The rate at which a specimen is functionalized depends on the surface flux of the reactive radicals. Dose rate can be estimated by analytical solution of the following partial differential equation describing the diffusional transport and first order or pseudo-first order reactive radical reaction processes:

$$k_c C(r, z) = D \frac{1}{r} \frac{\partial}{\partial r} r C(r, z) + \frac{\partial^2}{\partial z^2} C(r, z)$$

wherein $k_c$ is the rate constant for loss of reactive radical from the gas in the sidearm conduit from all first order processes, C is the concentration of the reactive radical, r is radial position of the specimen from the longitudinal axis of the sidearm conduit, and z is an axial position (distance from the sidearm conduit entrance to the main gas chamber) with the boundary conditions:

$$C(r, z) = C_o, \text{ at } z = 0; \text{ and}$$

$$-D \frac{\partial}{\partial z} C(r, z) = k_s C(r, z), \text{ at } z = z_1 \text{ (the specimen surface);}$$

wherein $k_s$ is the rate constant for loss of reactive radical at the specimen surface.

If $T_{diff} << T_{rcm}$, the partial differential equation simplifies to:

$$\frac{k_c C(z)}{D} = \frac{\partial^2}{\partial z^2} C(z).$$

A general solution to this has the form:

$$C(z) = A \exp[-(k_c/d)^{0.5} z] + B \exp[(k_c/D)^{0.5} z]$$

wherein A and B are constants determined by application of the boundary conditions as follows:

$$A = \frac{G_B C_O}{G_A + G_B};$$

$$B = \frac{G_A C_O}{G_A + G_B};$$

wherein:

$G_A = [D(k_c/D)^{0.5} - k_s] \exp[-(k_c/D)^{0.5} z_1];$ and
$G_B = [-D(k_c/D)^{0.5} + k_s] \exp[(k_c/D)^{0.5} z_1].$ The complete analytical solution for the case of no radial concentration dependence and first order reactive radical loss processes is as follows:

$$C(z) = \frac{C_o}{(G_A + G_B)} \{G_B \exp[-(k_c/D)^{0.5} z] + G_A \exp[+(k_c/D)^{0.5} z]\}$$

The reactive radical dose rate can thus be estimated, and it is readily appreciated that the dose rate can be increased dramatically by increasing the concentration of the reactive radical at the sidearm conduit entrance (at z=0), and affected by the material used to form the sidearm conduit and the specimen material. Total reactive radical doses of about $10^{24}$–$10^{26}$ cm$^{-2}$ day$^{-1}$ or more can be obtained with the reactor disclosed herein.

Using the reactor and operating conditions as described above, (specifically, 2 Torr total system pressure of aviators breathing oxygen as the source or working gas), an exposure time on the order of seconds (100–1,000) is typically sufficient to achieve essentially complete surface functionalization of a porous polyethylene disc (having, e.g., a thickness of $\frac{1}{16}$ inch (1.6 mm) and a diameter of 0.75 inch (19 mm) and a nominal pore size on the order of 20 microns). Reducing the exposure time can provide a partially functionalized specimen. However, degradation of such a disc using remote plasma treatment according to invention requires an exposure time on the order of hours (1–10) to achieve even a 5% mass loss. Thus, functionalization of even the innermost interstitial regions of a porous specimen is much faster than degradation of the specimen, using remote plasma treatment according to the invention.

SURFACE-FUNCTIONALIZED POROUS ARTICLES

The porous article having surface functionality according to the present invention may be obtained by treating a porous article as described above with remotely-generated gas-phase radicals, also as described above. The porous article has an exterior surface, a bulk matrix, and pores which extend from the exterior surface into the bulk matrix. The pores are surrounded by, and thus define, the pore surface. The bulk matrix and surface of the (pre-treated) article is formed, at least in part and preferably in whole, of organic polymer, i.e., polymers having carbon and hydrogen atoms.

When the gas-phase radicals reach the article and diffuse through the pores of the article, the exterior and interstitial surfaces become modified with functional groups such as amino, hydroxyl, carbonyl and carboxyl groups. The modification is the result of replacing hydrogen atoms that are part of the basic structure of the porous article, with oxygen or nitrogen atoms, to form hydroxyl carbonyl carboxylic acid groups or amino groups, respectively, depending on the identity of the source gas. The functional groups which are added to a surface according to the invention are hydrophilic. Thus, after sufficient functionalization of a hydrophobic polymer surface, all points on the surface may be made hydrophilic. However, the functionalization will not extend into the bulk matrix, but instead will be confined to the surface or, at most, the near surface region, so that the matrix is free from the hydroxyl, amino, etc. functional groups that have been added to the surface.

The organic polymer(s) which form the porous article are reactive with gas phase radicals, and will typically experience mass loss upon exposure to the radicals over an extended period of time. Mass loss typically occurs upon chain scission and subsequent ablation of carbon atoms. However, the polymer and treatment conditions are selected so that the rate of mass loss is relatively low compared to the rate at which functionality is introduced to the surface of the article. Accordingly, the polymer matrix, and particularly the interior bulk matrix of the article, is essentially unchanged by the treatment, and the supporting structure retains its bulk and mechanical properties. The present invention thus avoids contact between the article and high energy beams which have been used in the art to create reactive sites at the surface, and in the bulk matrix. Such beams typically cause chain scission within the bulk matrix of the article, thereby weakening the mechanical strength of the article. The present invention avoids this undesirable result, and provides an article with a bulk matrix that has not been modified by chain scission.

Generally, the diffusion of the gas-phase radicals from the exterior surface through the interstitial volume of the article proceeds in a distinct front. Behind the front, the interstitial surfaces of the pores become functionalized by the introduction of amino, hydroxyl, etc. groups. Ahead of the front, the pore surface retains its initial structure and functionality. When the reaction front is allowed to pass through the entirety of the article, the entire surface of the article gains functional groups.

The functionalized porous article according to the present invention may be characterized in several way. For example, scanning electron microscopy (SEM) may be used to monitor the structural effects of the remote gas-phase ion treatment on a solid support. Typically, complete surface functionalization of a porous polymer article can be achieved with no appreciable change in the surface morphology, where no appreciable change means that no change in morphology is observed as determined by scanning electron microscopy at a magnification of 50×, and preferably less than 2000×. However, if the porous article is exposed to an extended treatment with remote plasma discharge, one can observe some mass loss by SEM. For example, one can use SEM to determine if the treatment has modified the appearance of the pores on the exterior surface of the solid support. However, the average pore size of the functionalized products of the invention is essentially the same as in the porous articles that serve as the starting materials. Furthermore, the bulk density of the product of the invention is essentially the same as the bulk density of the precursor article. The porous nature of the precursor article is essentially unchanged by the process of the invention, except of course, for the addition of functional groups to the pore surfaces.

A relative measure of the amount of functionality that has been imparted to the surface of the porous article may be obtained by using any of x-ray photoelectron spectroscopy (XPS), infrared spectroscopy or chemical analysis. For many applications, the functionalized article is useful because the initially introduced functionality (e.g., amino or hydroxyl groups) provides chemical handles which may be elaborated into biomolecules and other application-specific chemical groups. Accordingly, the chemical reactivity of the surface, after treatment according to the invention, is a very useful descriptor of the articles of the invention.

To some extent, the reactivity of the surface is related to the amount of surface area: assuming uniform functionalization, the greater the surface area, the greater the amount of functional groups per gram of sample. For a porous article having a surface area of about 2,000 cm$^2$ per gram, functionalization according to the invention can provide about 0.01 to 1.0 μmoles of reactive functional group per gram of sample. Typical functionalization levels are 0.1 to 0.5 μmoles of reactive functional group per gram of sample, for a sample having a surface area of 2,000 cm$^2$ per gram as measured by mercury porosimetry or gas adsorption measurements. This corresponds to reactive surface functionality on the order of $10^{-12}$ to $10^{-10}$ moles/cm$^2$.

The amount of reactive surface functionality on a functionalized article according to the invention will depend on the conditions under which the chemical reactivity is measured. Some swelling of the porous article will occur if the article is placed into an appropriate solvent. The swollen surface will tend to be more reactive with chemical reagents because more of the initially introduced functional groups will be accessible to the chemical reagents.

The chemical reactivity of a modified surface according to the invention can be measured by many techniques. For example, the amount of reactive amino groups present on an aminated specimen may be determined chemically according to Allul, R. (DNA Probes, Keller, H. G. et al., Eds. Macmillan, New York (1993)). Thus, the aminated specimen is treated with 3-O-(4-nitrophenylsucciinylated)-5'-O-DMT-deoxyribonucleoside, followed by blockage of unreacted amines with pyridine/acetic anhydride/N-methyl imidazole (8:1:1, v:v:v). The amount of bound deoxyribonucleoside is determined by absorbance at 498 nm after treatment with 70% aqueous perchloric acid, toluenesulfonic acid in acetonitrile, commercial deblock preparations, or the like, to release the DMT group from the support.

In a preferred embodiment of the invention, a hydrophobic porous polymer article is treated with a substantially uniform concentration of reactive radicals, either atomic oxygen, hydroxyl or amino radicals, using remote plasma discharge to form a substantially uniform hydrophilic surface layer on the article. In a more preferred embodiment, the hydrophilic surface substantially comprises reactive hydroxyl functionality, while in another more preferred embodiment, the hydrophilic surface substantially comprises reactive amino functionality. The surface functionality is spread across the entire surface of the article, which includes the exterior surface and the pore surface. Complete surface functionalization can be detected and distinguished from partial surface functionalization by wicking experiments with water, at least when the untreated surface is hydrophobic.

When oxygen is used as the source gas, the surface-functionalized porous article of the invention may have hydroxyl, carbonyl and carboxyl groups at the surface. Preferably, hydroxyl groups are the predominate functional group at the article's surface. If the surface content of carbonyl and/or carboxyl groups is undesirably high, such a functionalized polymer may be treated with a reducing agent, e.g., lithium aluminum hydride or sodium borohydride, to reduce all or essentially all of the carbonyl and/or carboxyl groups to hydroxyl groups.

Thus, subsequent to being exposed to the discharge, the surface-functionalized porous article having carbonyl and carboxylic acid groups (possibly in addition to hydroxyl groups) may be reacted with a reducing agent, so that hydroxyl groups are the predominant functional group bonded to the polymers which form the surface of the article. In addition, or alternatively, chemical agents that react with and cap (neutralize, eliminate) surface free radical sites and/or peroxides may be contacted with the surface functionalized porous article. Such chemical agents include ammonia, dimethyl sulfide and other gases known in the art to cap/react with/neutralize free radical or peroxides on a polymer surface. Hindered amine light stabilizers, such as the Irganox™ products (e.g., Irganox™ 1076 and 1010) sold by Ciba-Geigy (Tarrytown, N.Y.) and and Cyanox™ 2246 from American Cyanamid (Wayne, N.J.), as well as antioxidants such as 2,6-di-tert-butyl-4-methylphenol (BHT) and Nonox™ CI from Imperial Chemical Industries, Great Britian, may also be used to cap these surface radicals or peroxides.

The functionalized porous article preferably has the following properties. It is inert in that it will not degrade upon contact with chemicals to which it is exposed when it is used as a solid-phase support for a synthesis procedure. It should be "sturdy" in that it maintains its integrity during use. Thus, the article should not break into pieces if, for example, it is placed into a solution with a rotating mechanical stirrer. Also, if placed into a tall column, the lower portion of the article should not become crushed and perhaps plug a screen that holds up the article (in instances where a screen is used to support the article).

Other properties are also desired. The article should have a high surface area to volume ratio. In other words, for a fixed volume of article, it is desired to maximize the surface area over which the functional groups may be added according to the present invention. The surface of the article should contain desirable "chemical handles" to which molecular fragments may be bonded, and should not contain any undesirable chemical groups which may interfere with a the utility of the article.

The functionalized polymeric articles of the invention are useful as supports for solid-phase organic synthesis, including the synthesis of biomolecules. However, the articles may in used in a number of other applications including, but not limited to, filtration media, carriers for immobilizing bioreactive components in bioreactor applications, chromatography media, media for distillation or extraction processes, and supports for diagnostic assays.

The following U.S. Patents and U.S. patent Applications are hereby incorporated herein by reference, in their entirety, for all purposes: U.S. application Ser. No. 08/254,361 filed Jun. 3, 1994, which is a continuation-in-part of U.S. application Ser. No. 07/857,901, filed Mar. 26, 1992 now U.S. Pat. No. 5,369,012 and Ser. No. 07/997,265, filed Feb. 23, 1993 now U.S. Pat. No. 5,332,551, which in turn is a division of U.S. application Ser. No. 07/894,505, filed Jun. 2, 1992, now U.S. Pat. No. 5,215,790, which in turn is a division of U.S. application Ser. No. 07/429,739, filed Oct. 31, 1989, now U.S. Pat. No. 5,141,806.

The following specific examples serve to further illustrate the invention. These examples are merely illustrative of the invention and are not to be construed as a limitation thereof.

EXAMPLE 1

A polytetrafluoroethylene reinforced silicone membrane sold under the trade name SILON by Bio-Med Sciences, Inc. of Bethlehem, Pa. is uniformity treated with atomic oxygen in an atomic oxygen reactor having a specimen holding sidearm. Operating conditions are shown in Table 1. The membrane initially has a hydrophobic surface which after treatment acquires hydrophilic hydroxyl functionality as follows:

Discs were similarly exposed to $5 \times 10^{14}/cm^3$ atomic oxygen atoms in the sidearm reactor for periods of time ranging from three seconds to ten minutes to characterize development of hydrophilicity as reflected in the amount of water uptake of the exposed samples. An amount of water sufficient to wet the hydrophilic portion was dropped onto the surface of each disc, and any excess was removed by pipet. The increase in mass due to water uptake was recorded, and the results based on an average of three specimens are presented in Table 3.

|  | Before | After |
|---|---|---|
| Surface | $-[Si(CH_3)_2-O-Si(CH_3)_2]_n- + 180$ | $-[Si(OH)_2-O-Si(OH)_2]_n- + 6H_2O + 4CO_2$ |
| Sub-Surface | $-[Si(CH_3)_2-O-Si(CH_3)_2]_n-$ | $-[Si(CH_3)_2-O-Si(CH_3)_2]_n-$ |

| | |
|---|---|
| Pressure (Pa) | 27 |
| Temperature (K) | 298 |
| Gas Mixture | 10% $O_2$ in Ar |
| C(z) (AO/cm$^3$) | $4 \times 10^{14}$ |

EXAMPLE 2

Discs of porous and nonporous high density polyethylene (HDPE) were treated with atomic oxygen to evaluate mass loss and the development of hydrophilicity. The porous polyethylene discs were cut from 1.6 rmm (¹/₁₆-in.) thick specimens obtained from Porex Technologies (Fairburn, Ga.) and had coarse, medium and fine pores with respective nominal pore diameters of about 250 μm, 49–90 μm, and 10–20 μm. The nonporous HDPE was obtained in the form of a 0.025 mm (1 mil) film. The discs had a diameter of about 19 mm (0.75 in.) and were cleaned by rinsing in a mixture of 1,1,1-tiichloroethylene and ethanol and drying in a vacuum overnight.

Duplicate sets of the discs were placed in the sidearm reactor of Example 1 and exposed to an atomic oxygen concentration of $5 \times 10^{14}/cm^3$. The weight of each disc was recorded at periodic intervals over a total exposure time of 12–15 hours to monitor mass loss. The results are presented in Table 2. In addition, scanning electron micrographs (SEM) of discs exposed to $3.6 \times 10^{14}/cm^3$ atomic oxygen atoms in the sidearm reactor for 166.25 hours were taken for comparison to unexposed material. As seen from the data in Table 2, the rate of mass loss varied according to material pore size, i.e., the larger the pore diameter, the greater the mass loss rate. Apparently, the mass loss rate depends mostly on the amount of surface area available for reaction, and not on diffusion. Estimates of the effective surface area of the discs calculated from the loss rate relative to the nonporous HDPE were corroborated from surface area estimates by SEM. The SEM also showed rounding of particles in the coarse pores and visible pitting in the medium and fine pores, with changes occurring uniformly across the thickness of the discs.

TABLE 2

| | Sample Weight (mg) | | | |
|---|---|---|---|---|
| Time (hours) | Disc #1 | Disc #2 | Disc #1 | Disc #2 |
| | HDPE Sheet (1 mil) | | POREX, Medium (49–90 μm) | |
| 0.0000 | 6.8223 | 6.7433 | 226.8562 | 229.1452 |
| 1.833 | 6.4403 | 6.3288 | 225.2864 | 227.5929 |
| 4.0667 | 6.1962 | 6.0763 | 224.4133 | 226.7565 |
| 5.8834 | 5.9684 | 5.8701 | 223.6999 | 226.0678 |
| 7.8001 | 5.7616 | 5.6614 | 223.0172 | 225.3709 |
| 9.7834 | 5.5604 | 5.4508 | 222.3613 | 224.6970 |
| 11.7834 | 5.3590 | 5.2480 | 221.6863 | 223.9940 |
| 14.2834 | 5.1219 | 5.0195 | 220.9277 | 223.2801 |
| | POREX, Fine (10–20 μm) | | POREX, Coarse (250 μm) | |
| 0.0000 | 254.0969 | 253.5941 | 451.5491 | 454.2949 |
| 1.6167 | 253.0543 | 252.7013 | 450.7072 | 453.0781 |
| 3.6167 | 252.4069 | 252.0329 | 449.8757 | 451.7606 |
| 5.6167 | 251.7920 | 251.4103 | 449.2417 | 451.1571 |
| 7.1000 | 251.2774 | 250.9041 | 448.5435 | 450.6771 |
| 9.1000 | 250.5556 | 250.1976 | 447.8187 | 449.7215 |
| 11.1167 | 249.9119 | 249.5267 | 446.7887 | 449.0990 |
| 12.8500 | 249.3742 | 248.9901 | 445.5790 | 448.0119 |

As seen from these data, the amount of water uptake increased linearly until the saturation level was reached. The development of hydrophilicity clearly occurred prior to observation of any mass loss, and appeared to be dependent on the rate of diffusion of the atomic oxygen through the porous solid. As the pore size increased, the diffusion rate also increased. Also, dyeing of the specimens using a water soluble dye showed that a distinct reaction front progressed through the porous material. The partially hydrophilicized samples had a distributed pore chemistry, the portion ahead of the reaction front remaining hydrophobic while the portion behind the reaction front was hydrophobia.

TABLE 3

| POREX, Fine (10–20 μm) | | POREX, Medium (49–90 μm) | | POREX, Coarse (250 μm) | |
|---|---|---|---|---|---|
| Time Exposed (sec) | Water Absorbed (% of disc wt) | Time Exposed (sec) | Water Absorbed (% of disc wt) | Time Exposed (sec) | Water Absorbed (% of disc wt) |
| 5 | 1.9 | 3 | 5.2 | 2 | 4.6 |
| 10 | 8.4 | 5 | 6.7 | 4 | 14.0 |
| 15 | 10.4 | 10 | 12.1 | 6 | 17.3 |
| 20 | 11.6 | 10 | 12.7 | 10 | 25.8 |
| 30 | 14.0 | 15 | 18.9 | 15 | 36.5 |
| 40 | 18.0 | 20 | 18.9 | 15 | 36.5 |
| 50 | 20.1 | 30 | 34.0 | 22 | 47.3 |
| 70 | 23.2 | 40 | 41.8 | 40 | 53.4 |
| 90 | 24.3 | 60 | 48.0 | 60 | 54.1 |
| 120 | 32.9 | 90 | 64.8 | 90 | 52.6 |
| 180 | 47.0 | 120 | 68.0 | | |
| 300 | 55.7 | 150 | 74.3 | | |
| 600 | 65.9 | 180 | 75.0 | | |
| 700 | 65.2 | 210 | 79.5 | | |
| | | 240 | 82.8 | | |

EXAMPLE 3

In a third example 4 samples of a porous solid consisting of UHMWPE and having a 7 micron nominal pore size, and of 0.025 inches thickness, was exposed to ammonia FDRC conditions in a side-arm reactor of the type described above for periods of time ranging from 30 minutes to 3 hours and at temperatures of 1) 25° C., 2) 50° C., and 3) 80° C., at a total pressure of 2.06 Torr with the plasma source on and 1.93 Torr with the plasma source off. At the end of the FDRC treatment period, the plasma source is turned off and the porous material is further treated by a 30 minute soak in the ammonia—argon gas at a total pressure of 400 Torr. The reactor was essentially identical to the side-arm reactor described above. The mass flow rate of the 10 percent ammonia in argon working gas was 132 standard cubic centimeters of gas per minute. The plasma source was an air-cooled Evenson cell operated at 70 Watts of forward RF power and 3 Watts of reflected RF power at 2.45 GHz.

Surface analysis by X-ray photoelectron spectroscopy showed that amines (alkyl substituted) had been introduced to the molecular surface of the 7 micron pore size UHMWPE at levels on the order of 20 atom percent with little dependence on sample temperature. In contrast, reflectance FTIR on identical specimens showed no detectable alkyl amine features. Together, the X-ray photoelectron and FTIR data show that the FDRC amination reaction is confined to the molecular surface of the porous polymer.

In addition, amine selective molecular probes such as fluorescein isothiocyanate (FITC) and fluorescein dichlorotriazine (DTAF) react with all functionalized surfaces throughout the porous polyethylene article, while being unreactive with the unmodified surfaces. Cleavage of the isothiourea formed by reaction of FITC with alkyl amine functions with aqueous 0.1 M NaOH releases fluorescein into solution for direct spectrophotometric measurement and calculation of the number of micromoles of amine function per gram of porous solid, which ranged between 0.2 and 0.5 micromoles of reactive amine per gram of the subject porous UHMWPE with 7 micron nominal pore size, after ammonia FDRC.

Additional measurements of pore surface alkyl amine content of 7-micron-pore-size porous UHMWPE after reaction under various conditions of time and temperature in an ammonia FDRC environment like that described above resulted in surface amine concentrations of 0.4 micromoles per gram.

EXAMPLE 4

A sample of 7 micron pore size porous UHMWPE, of 0.025 inches in thickness, was subjected to atomic oxygen FDRC conditions for at least one hour in a side-arm reactor as described above, with operating conditions similar to Example 3 except that aviators breathing oxygen was used as the working gas. No significant pressure rise was observed on plasma source ignition, as is characteristic of atomic oxygen FDRC.

Direct measurement of surface R—OH concentrations using the molecular probe D-1557 sulfonyl chloride from Molecular Probes Inc., Eugene Oreg., showed 0.03 micromoles of R—OH per gram sample, after base hydrolysis (which releases the chromophore) of the sulfonic acid ester formed by reaction of the D-1557 probe (1 mg/ml in dry acetone with 1.0% pyridine) of the functionalized polymer surface.

A second identical sample of the functionalized porous UHMWPE was reacted with: 1) the D-1557 probe (1 mg/ml in dry acetone, 1% pyridine) followed by, 2) thorough washing with dry acetone and, 3) reaction with a 20 wt % solution of a 4 generation PAMAM Starburst™ dendrimer (amino terminated) for 3 days. The terminal amino groups on the dendrimer react with the sulfonic acid esters formed by reaction of D-1557 with the surface R—OH groups to produce D-NH-(dendrimer), thereby immobilizing the dendrimer on the surfaces of the oxygen FDRC porous polymer. Subsequent analysis of the oxygen FDRC porous polymer using the FITC method of Example 3 above revealed that on the order of 0.2 micromoles per gram of primary amine function had been introduced by coupling the dendrimer to the surface.

The invention provides new types of solid-phase supports for the separation and purification of organic and biochemicals by adsorptive, absorptive and chromatographic processes. The present invention permits the realization of novel, useful and practical separation media which cannot be achieved using the methods of the prior art. The invention also provides new types of solid phase supports for chemical syntheses.

While the invention has been described in terms of specific embodiments, it is evident in view of the foregoing description that numerous alternatives, modifications and validations will be apparent to those skilled in the art. Thus, the invention is intended to encompass all such alternatives, modifications and variations which fall within the scope and spirit of the invention and the appended claims.

What is claimed is:

1. A porous article having an exterior surface, a bulk matrix and pores extending from the exterior surface into the bulk matrix, wherein the pores define an interstitial surface, wherein the bulk matrix is formed, at least in part, of an organic polymer comprising carbon and hydrogen atoms, and the exterior and interstitial surfaces are formed, at least in part, of the organic polymer comprising carbon and hydrogen atoms wherein some of the hydrogen atoms are replaced with functional groups selected from amino, hydroxyl, carbonyl, and carboxylic acid, wherein the functional groups are directly bonded to the organic polymer of the bulk matrix, and wherein the exterior surface does not display appreciable surface roughness, according to SEM analysis, due to ablation of surface carbon atoms or chain scission.

2. The porous article of claim 1 wherein amino groups are directly and covalently bonded to the polymers which form the interstitial surface.

3. The porous article of claim 1 wherein the functional groups are predominantly hydroxyl groups.

4. The porous article of claim 1 wherein the polymers which form the bulk matrix comprise polyolefin, and the polymers which form the exterior and interstitial surfaces comprise hydroxyl-substituted polyolefin.

5. The porous article of claim 1 wherein the polymers which form the bulk matrix comprise polyolefin and the polymers which form the exterior and interstitial surfaces comprise amino-substituted polyolefin.

6. The porous article of claim 1 having a void volume of from 1% to 90%.

7. The porous article of claim 1 having a void volume of from about 35% to 60%.

8. The porous article of claim i having an effective pore diameter of about 0.01 microns to 2000 microns.

9. The porous article of claim 1 having an effective pore diameter of about 1 to about 50 microns.

10. The porous article of claim 1 in the form of a membrane.

11. The porous article of claim 1 wherein the bulk matrix is formed from sintered polyolefin.

12. The porous article of claim 1 wherein the average pore size on the exterior surface is within 1% of the average pore size within the matrix of the article.

13. The porous article of claim 1 which is hydrophilic at all points of the surface.

14. The porous article of claim 1 having surface functionality in the amount of $10^{-12}$ to $10^{-10}$ moles/cm$^2$.

15. A surface-functionalized porous article prepared by a process comprising the steps of:

providing a precursor porous article having an exterior surface, an interstitial surface and a bulk matrix, the surfaces and bulk matrix both comprising organic polymers; and exposing the precursor porous article to remote discharge formed by radical forming conditions acting on a source gas, the source gas selected from the group consisting of oxygen, ammonia and a mixture of nitrogen and hydrogen, under reaction conditions such that radicals from the discharge react with the surfaces of the precursor porous organic article to cause direct covalent bonding of functionality to the surfaces, the functionality selected from the group consisting of amino, hydroxyl, carbonyl and carboxyl groups.

16. The surface-functionalized porous article of claim 15 wherein the discharge is a plasma discharge.

17. The surface-functionalized porous article of claim 15 wherein precursor porous article comprises polyethylene.

18. The surface-functionalized porous article of claim 15 wherein the precursor porous article comprises sintered particles of non-porous polyethylene.

19. The surface-functionalized porous article of claim 15 wherein the precursor porous article has a pore volume of 35% to 60%.

* * * * *